United States Patent
Wuepper et al.

(10) Patent No.: US 11,538,150 B2
(45) Date of Patent: Dec. 27, 2022

(54) METHOD OF DETECTING SYMPTOMS OF PERITONITIS

(71) Applicant: FRESENIUS MEDICAL CARE DEUTSCHLAND GMBH, Bad Homburg (DE)

(72) Inventors: Andreas Wuepper, Buettelborn (DE); Ulrich Moissl, Karben (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 817 days.

(21) Appl. No.: 16/315,630

(22) PCT Filed: Jul. 7, 2017

(86) PCT No.: PCT/EP2017/000803
§ 371 (c)(1),
(2) Date: Jan. 5, 2019

(87) PCT Pub. No.: WO2018/007013
PCT Pub. Date: Jan. 11, 2018

(65) Prior Publication Data
US 2019/0228526 A1  Jul. 25, 2019

(30) Foreign Application Priority Data
Jul. 7, 2016 (DE) .............. 10 2016 008 332.8

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0075* (2013.01); *A61B 5/0077* (2013.01); *A61B 5/4222* (2013.01); *A61B 5/6898* (2013.01); *A61M 1/1605* (2014.02); *A61M 1/28* (2013.01); *G06T 7/90* (2017.01); *H04M 1/04* (2013.01); *A45C 2011/002* (2013.01);
(Continued)

(58) Field of Classification Search
CPC ................ A61M 1/1605; G16H 10/20; A45F 2200/0516
See application file for complete search history.

(56) References Cited

U.S. PATENT DOCUMENTS

| | | | |
|---|---|---|---|
| 2007/0059687 A1* | 3/2007 | Ohno | C12Q 1/689 435/372 |
| 2008/0183127 A1 | 7/2008 | Landherr | |

(Continued)

FOREIGN PATENT DOCUMENTS

| | | |
|---|---|---|
| CN | 201657912 | 12/2010 |
| DE | 102012020945 | 4/2014 |

(Continued)

*Primary Examiner* — Fabricio R Murillo Garcia
(74) *Attorney, Agent, or Firm* — Jacobson Holman PLLC

(57) ABSTRACT

The invention relates to a method of detecting symptoms of peritonitis, wherein the method comprises the following steps:
taking a photo of a drainage solution and/or of a catheter exit site using a smartphone and/or inputting at least one query parameter which is input by a patient through the input zone of a smartphone; and,
evaluating the photo and/or the query parameter.

13 Claims, 1 Drawing Sheet

Figures 1A, 1B, 1C, 1D:
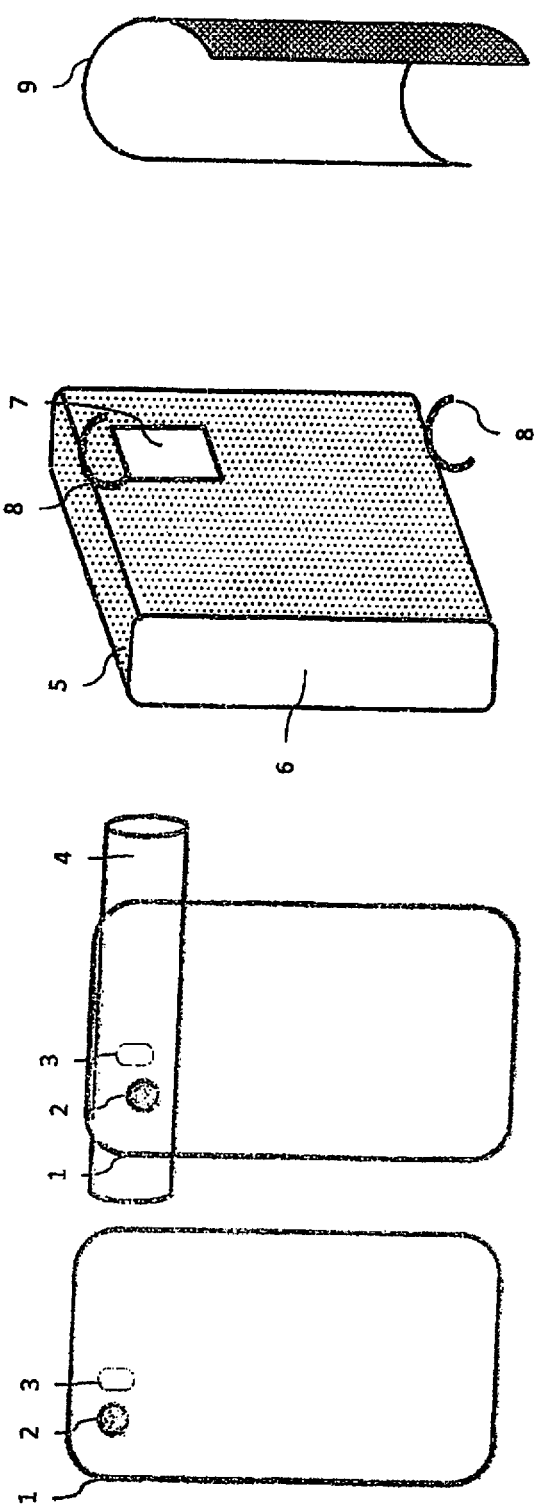

(51) Int. Cl.
*A61M 1/28* (2006.01)
*A61M 1/16* (2006.01)
*G06T 7/90* (2017.01)
*H04M 1/04* (2006.01)
*A45C 11/00* (2006.01)
*A61B 5/145* (2006.01)
*G03B 17/56* (2021.01)
*G16H 10/20* (2018.01)
*G16H 30/40* (2018.01)
*G16H 40/63* (2018.01)
*H04M 1/72409* (2021.01)

(52) U.S. Cl.
CPC ......... *A61B 5/0013* (2013.01); *A61B 5/14507* (2013.01); *A61M 2205/3306* (2013.01); *G03B 17/566* (2013.01); *G06T 2207/10024* (2013.01); *G06T 2207/30104* (2013.01); *G16H 10/20* (2018.01); *G16H 30/40* (2018.01); *G16H 40/63* (2018.01); *H04M 1/72409* (2021.01); *H04M 2250/52* (2013.01)

(56) References Cited

U.S. PATENT DOCUMENTS

| | | | |
|---|---|---|---|
| 2009/0036175 A1* | 2/2009 | Brandenburg | A45F 5/02 455/575.1 |
| 2009/0149776 A1 | 6/2009 | Adams | |
| 2013/0131574 A1* | 5/2013 | Cosentino | A61M 1/1605 604/6.07 |
| 2013/0165847 A1* | 6/2013 | Scarpaci | H05B 1/025 417/478 |
| 2015/0264241 A1* | 9/2015 | Kleekajai | H04N 5/335 348/227.1 |
| 2016/0157736 A1* | 6/2016 | Huang | A61B 5/0059 600/476 |
| 2018/0142828 A1* | 5/2018 | Reichel | B32B 17/10 |
| 2018/0352060 A1* | 12/2018 | Gifford | H04M 1/21 |
| 2019/0216859 A1* | 7/2019 | Meron | A61K 35/74 |
| 2020/0016301 A1* | 1/2020 | Kleiner | A61F 13/00068 |

FOREIGN PATENT DOCUMENTS

| | | |
|---|---|---|
| DE | 102012021805 | 5/2014 |
| TW | 1525578 | 3/2016 |
| WO | WO 99/06082 | 2/1999 |
| WO | WO 2009/094034 | 7/2009 |
| WO | WO 2012/087152 | 6/2012 |
| WO | WO 2012/155067 | 11/2012 |

\* cited by examiner

METHOD OF DETECTING SYMPTOMS OF PERITONITIS

The invention relates to a method of detecting symptoms of peritonitis.

Peritonitis can occur as a complication in peritoneal dialysis patients (PD patients) and represents a serious health risk. It can result in a failure of the suitability of the peritoneum for dialysis ("technique failure") and can make a change of the type of treatment to hemodialysis necessary.

The rate of peritonitis associated with peritoneal dialysis is typically one incidence per patient every 20 to 38 months. The mortality rate is consequently approximately 3% and the technique failure approximately 15%.

Peritoneal dialysis peritonitis (PD peritonitis) presents as a cloudy drainage solution, so-called "cloudy effluent" (99%). Symptoms are furthermore present such as abdominal pains (95%), nausea/vomiting (30%) or constipation/diarrhea (15%).

Antibiotics are administered intraperitoneally and orally as a therapy. Said therapy is started immediately as a rule on the occurrence of cloudy effluent, even before the results of the cell culture are available. An early recognition of peritonitis allows an early start of treatment and thus better prognoses for a cure and a limitation of complications.

Peritoneal dialysis (PD) is a home therapy which can be performed by the patient himself without the presence of a physician or a nurse. The patient has to watch for signs of peritonitis himself.

Against this background, it is the object of the invention to assist a patient in the recognition of signs of peritonitis.

This object is achieved in accordance with the invention by a method of detecting symptoms of peritonitis, the method comprising the following steps: taking a photo of a drainage solution and/or of a catheter exit site using a smartphone and/or inputting at least one query parameter which is input by a patient through the input zone of a smartphone; and evaluating the photo and/or the query parameter.

More than one photograph can also be evaluated in accordance with the invention. If the term photograph is used here, it should also be understood as the use of more than one photograph.

The evaluation can comprise correlating the photos taken by the patient or the query parameters input by the patient with corresponding reference values of healthy patients not suffering from peritonitis.

After the evaluation of the photos and/or of the query parameter, an indication can, for example, be output to the patient which explains the symptoms of peritonitis to him and/or an indication of the likelihood of a presence of peritonitis can be given.

The likelihood can be calculated in dependence on the taken photographs or on the input query parameters. For this purpose, within the framework of the method, corresponding reference values, comparison tables or other reference data can be stored with which the taken photographs and/or the query parameters can be compared. The self-diagnosis can be made easier for the patient on this basis.

In the evaluation of the photographed drainage solution, it can in the present case be the drainage solution exiting the abdomen of a patient which may be cloudy in the case of peritonitis and which can hereby provide the patient with information on the presence of peritonitis.

It is conceivable in a preferred embodiment that in accordance with the method a taking of a photograph is carried out with the principle of scattered light measurement in that a brightness value and/or a color value is calculated in averaged form, in particular over the total pixel range or over a partial range thereof of the camera or of the smartphone. This averaged value can be correlated with a reference value or threshold value and the finding of peritonitis can thus be made easier for the patient. It is alternatively or additionally also conceivable that the photograph and/or the query parameters are sent in accordance with the method to a qualified physician or nurse by means of the smartphone and the result of the evaluation of the photograph or of the query parameters carried out by the physician or nurse is in turn communicated to the user of the method in accordance with the method.

It is conceivable in a further preferred embodiment that the scattered light measurement takes place in reflection. For this purpose, a light source and the camera of the smartphone can be provided directly adjacent at the smartphone such that, on a corresponding illumination of the catheter exit site, of the drainage solution or of the drainage bag or drainage hose, the scattered light reflected by the illuminated object can be detected and evaluated.

It is conceivable in a further preferred embodiment that in accordance with the method an image recognition of the photograph is made. For this purpose, a photo can be taken by means of the photo camera with or without LED light or flash and individual regions of the image or the total image can thereupon be evaluated using image recognition and, for example, compared with reference images. Specific color values or brightness values of the photo can be compared with predefined parameters in the image recognition, with, for example, a recognized cloudiness of the dialysis solution or a redness of the catheter exit site being able to be specifically displayed to the patient. As mentioned above, an alternative or additional sending of the photograph for evaluation by a physician is also conceivable.

It is furthermore conceivable in a further preferred embodiment that the photograph is a photo of the drainage solution within a hose or a bag of a peritoneal dialysis machine. A user or a patient can thus inspect the drainage solution for peritonitis which may be present and which is frequently indicated by a cloudiness of the dialysis fluid in a simpler and independent manner during the independent carrying out of peritoneal dialysis by means of a peritoneal dialysis machine. It is not necessary for this purpose to comprehensively modify the actual peritoneal dialysis machine, but a user can rather use his own smartphone by installing computer software for a self-diagnosis on his own smartphone which carries out the method accordingly.

It is furthermore conceivable in a further preferred embodiment that at least one marking is used at the hose and/or at the bag for the evaluation of the photograph of the drainage solution. Markings can thus, for example, be designed at the lower side of the bag and can be made with lines of different thickness. The smartphone can in this respect be positioned at the upper side of the bag and the lower side can be photographed through the bag and through the drainage solution contained therein. The degree of visibility of the markings can be evaluated in an automated manner by means of the method in accordance with the invention and can serve as a measure for the cloudiness of the drainage solution. Markings can additionally or alternatively also be applied to the upper side of the bag which facilitate the image recognition and which minimize the influence of the spacing of the camera from the bag as well as the orientation of the camera relative to the bag.

Provision can furthermore be made in a further preferred embodiment that two regions of the hose are evaluated by means of photographs, with one region corresponding to the inlet and one region corresponding to the outlet of a peritoneal dialysis machine. The hose can in this respect be a single-piece hose section or two part-hoses can also form the inlet and the outlet of the peritoneal dialysis machine and can be evaluated in accordance with the invention.

The invention furthermore relates to a computer program, in particular to an app, for a smartphone having a photo camera and an input zone, in particular for carrying out a method in accordance with one of the claims 1 to 8 by means of a smartphone. The method in accordance with one of the claims 1 to 8 can be carried in an analog manner by a smartphone with the computer program so that the features of claims 9 to 15 correspond to the respective features of claims 1 to 8. The details and advantages each correspond in this respect so that repeating them can be dispensed with.

The term app here means a computer program which is intended for use on a mobile electronic device. The mobile electronic device can in particular be a smartphone, a tablet or a similar device which typically comprises a photo camera, an illumination and an input zone for inputting information by an operator.

The invention furthermore relates to a smartphone having a photo camera, an input zone and having a computer program for detecting symptoms of peritonitis in accordance with one of the claims 9 to 15 and/or having a processor for carrying out the method in accordance with one of the claims 1 to 8.

The invention is also directed to a holding apparatus in accordance with claim 17 for a smartphone, in accordance with claim 16, having a holding region for holding the smartphone, a hose holding region for holding a hose and a window which is configured to enable the photographing of a hose held in the hose holding region by means the smartphone held by the holding region. The hose holding region can also be configured to hold two or more hoses or hose sections and to enable a corresponding photographing of the hoses. It advantageously enables the named holding apparatus to couple a smartphone simply and protected from light with a hose which is to be photographed and evaluated and which has a corresponding drainage solution.

It is conceivable in a particularly preferred embodiment that a lightproof hose cover is provided which can be coupled to the holding apparatus such that a region or hose photographed by means of the smartphone is protected from light or is shaded. The quality of the photographs can hereby be kept constant or more constant independently of external light conditions. The determining of peritonitis in accordance with the invention is thus also improved.

Further advantages and details of the invention are explained with reference to the embodiment shown by way of example in the Figures. There are shown:

FIG. 1a: a rear view of a smartphone in accordance with the invention;

FIG. 1b: a rear view of a smartphone in accordance with the invention with a hose;

FIG. 1c: a holding apparatus in accordance with the invention; and

FIG. 1d: a lightproof hose seal.

FIG. 1a shows a smartphone 1 in accordance with the invention having a camera lens 2 or having a photo camera 2, having an LED light/flash 3 and having an input zone provided at the side typically disposed opposite the camera lens 2 or having a corresponding input zone for inputting information. The input zone can in this respect typically be designed as a touch screen.

FIG. 1b shows the smartphone 1 of FIG. 1a having a hose 4 which is disposed upstream of the camera lens 2 and which can be the hose of a peritoneal dialysis machine for conducting a drainage solution. The hose 4 is here arranged directly in front of the camera lens 2 and can thus be detected by the photo camera. The hose 4 can in particular be arranged such that the total region detected by the photo camera 2 is filled by the hose 4. This can be facilitated by coupling the hose 4 and the smartphone 1 to a holding apparatus 5.

FIG. 1c shows an apparatus for scattered light measurement at the hose 4 or a holding apparatus 5 mentioned above for holding a smartphone 1. The smartphone 1 can be introduced into the holding apparatus 5, for example, via an opening 6 for receiving the smartphone 1. An embodiment is, however, also conceivable in which the smartphone 1 is not introduced into the holding apparatus 5, but is rather only fastened thereto or coupled thereto. A window 7 can be provided at the holding apparatus 5 and the camera lens 2 and the LED light/flash 3 can be directed through it onto a hose 4 arranged before or next to said LED light/flash. The hose 4 can be held by means of a hose holder 8 in the region of the window 7. A more complex embodiment of the holding region is, however, also conceivable in which two or more hoses 4 or hose sections can be held in the region of the window 7.

FIG. 1d shows a lightproof hose cover 9 which can be coupled to the holding apparatus 5 and/or to the hose 4 such that a region of the hose 4 photographed by means of the smartphone 1 is shaded. More stable light conditions in the imaged region and thus better evaluations of the photographs can hereby be provided.

In the embodiment of the invention, the measurement principles of scattered light measurement and image recognition are possible.

With scattered light measurement, the camera 2 of the smartphone 1 is held directly toward the measured object, for example the hose or the bag. The LED or the flash 3 lights up for the measurement and their light is scattered at the cloudy solution located in the measured object and is incident onto the camera. A brightness value or color value is evaluated while averaged over the total pixel range of the camera 2.

The determined value is correlated with a reference value or threshold value which is measured, for example, at the hose piece which is filled with a clear solution, e.g. the supplied peritoneal dialysis solution.

The intensity of the light or color is proportional to the cloudiness/coloring of the solution. Since the LED 3 and the camera 2 are directly adjacent with a smartphone 1, the scattered light measurement can take place in reflection.

A photo is taken for image recognition (with or without LED/flash 3). Individual regions of the image are evaluated using image recognition.

The hose or the bag are possible as measurement sites with both measurement principles. Possible embodiments therefore comprise:

a combination of a scattered light measurement with a measurement at the hose, with there ideally being an auxiliary apparatus or holding apparatus 5 which ensures a fixed position of the smartphone 1 with respect to the hose 4 by clips 8 or hose holding regions 8 at the hose 4. In addition, the auxiliary means 5 has a reception opening 6 through which the smartphone 1 is pushed, whereby it can be fixed at the hose 4 such that the LED 3 and the camera 3 directly contact the hose 4. The apparatus has a window 7 which allows light to pass to the hose 4 for the LED 3 and the camera 2. The auxiliary apparatus 5 is composed of a light-impermeable material and screens external light from the measurement path. A hose cover 9 serves for screening the hose 4 from external light in the region of the measurement path and beyond.

A calibration at an empty hose 4 can take place before the measurement at the outflowing drainage.

A combination of image recognition with a measurement or with a photograph at the bag is also conceivable. The patient photographs the bag after a complete drainage. There are the following options for an evaluation:

on the one hand, an automated comparison of the image with a library of images can be carried out. On the other hand, there can be markings on the lower side of the bag, optionally of different line thicknesses. The degree of visibility of the markings is automatically evaluated and is deemed a measurement for the cloudiness. In addition, markings can likewise be attached to the upper side of the bag; they facilitate the image recognition and minimize the influence of the spacing of the camera 2 from the bag and the orientation of the camera 2 relative to the bag. In addition, the cloudiness could be evaluated by the difference of the sharpness/brightness between the markings on the upper side and on the lower side.

A further measure may be the application of a white field for the white balance to be able to evaluate color information in order, for example, to detect a color change of the dialyzate.

A combination of a scattered light measurement with a measurement at the bag is furthermore conceivable. Due to the flexibility of the bag, a direct placing of the smartphone 1 onto the bag is, however, not as easily reproducible as the attachment to the hose 4. In addition, the screening of external light is more difficult due to the size and properties of the bag.

A combination of image recognition with a measurement at the hose is furthermore conceivable. In this respect, the smartphone 1 can be fixed to a point at which it detects both the inflow and the outflow. The inflow can in this respect serve as a reference value and the cloudiness of the outflow can be measured relative thereto.

The following combinations are possible for validating the suspicion of peritonitis:

a trend analysis of the degree of cloudiness, with an increase in cloudiness over consecutive bag changes being a strong indication of peritonitis.

A combination of a measurement of the cloudiness with queries of symptoms of the patient.

A comparison of the degree of scattered light or of the level of cloudiness with a threshold value or with a transition region, e.g. there may be a histogram of values in patients without peritonitis and a histogram of patients with peritonitis. Both histograms may overlap. The transition region or a fixed threshold value would then be in the overlap region.

Symptoms such as abdominal pain, nausea, rising body temperature or feeling of a fever, constipation and diarrhea can be regularly queried by the smartphone 1 or by the computer program or method to obtain an initial suspicion of peritonitis. These symptoms can thus represent the query parameters in accordance with the invention.

In accordance with the invention, a single symptom or a combination of the named symptoms can be queried in this context.

In addition, on suspicion of peritonitis due to a positive cloudiness measurement, the symptom query can be carried out ad hoc to validate the suspicion.

Provision can furthermore be made that the catheter exit site of the peritoneal dialysis machine is photographed and evaluated by means of the computer program or in accordance with the method, for example on a justified suspicion of the patient. The photograph of the catheter exit site can here be evaluated automatically via an image comparison with stored images and can alternatively or additionally be sent as a telemedical application to a supervising physician or nurse for evaluation. In particular exit-site infections can be recognized. An exit-site infection is typically characterized by reddening, swelling and tenderness on palpitation in the region of the catheter exit site. These infections may only be superficially present or may also extend into subcutaneous areas.

The invention claimed is:

1. A method of detecting symptoms of peritonitis in a patient, wherein the method comprises steps of:

taking a photo at a specific region of a hose conducting a drainage solution, flowing from inside the patient, using a smartphone having a camera and an input zone for inputting at least one query parameter by the patient through the input zone of the smartphone;

evaluating the taken photo and evaluating the at least one query parameter when inputted, wherein a lightproof hose cover is coupled to a holding apparatus, where the smartphone is introduced, such that the specific region of the hose photographed by the smartphone camera is protected from light or is shaded, and wherein taking the photo is carried out such that a brightness value of the taken photo is calculated averaged over a total or partial pixel range of the smartphone camera, wherein the holding apparatus and the lightproof hose cover do not cover the smartphone camera when the hose is placed in a holder of the holding apparatus to allow the taking of the photo of the specific region of the hose; and detecting the symptoms of peritonitis by comparing a degree of scattered light detected at the taken photo at the specific region with a threshold value of peritoneal dialysis solution supplied to the patient.

2. The method in accordance with claim 1, characterized in that the scattered light measurement takes place in reflection.

3. The method in accordance with claim 1, characterized in that an image recognition of the photo is carried out.

4. The method in accordance with claim 1, characterized in that the hose is of a peritoneal dialysis machine.

5. The method in accordance with claim 4, characterized in that at least one marking is used at the hose for evaluation of the photograph of the drainage solution.

6. The method in accordance with claim 1, characterized in that two regions of the hose are evaluated by photographs, with one region corresponding to an inflow and one region corresponding to an outflow of a peritoneal dialysis machine.

7. A non-transitory computer readable storage medium for a smartphone having a photo camera and an input zone, for recognizing symptoms of peritonitis, wherein the medium carries a program that evaluates at least one photograph taken at a specific region of a hose conducting a drainage solution, flowing from inside a patient, by the smartphone camera and evaluates the taken photo and at least one query parameter input by the patient via the input zone, and wherein a lightproof hose cover is coupled to a holding apparatus where the smartphone is introduced such that the specific region of the hose photographed by the smartphone camera is protected from light or is shaded, and wherein taking the photo is carried out such that a brightness value of the taken photo is calculated averaged over a total or partial pixel range of the smartphone camera, wherein the holding apparatus and the lightproof hose cover do not cover the smartphone camera when the hose is placed in a holder of the holding apparatus to allow the taking of the photo of the specific region of the hose.

8. The non-transitory computer readable storage medium in accordance with claim 7 programed to carry out taking a photograph in accordance with a principle of a scattered light measurement in that the program calculates a brightness value and/or a color value averaged over a total or partial pixel range of the camera.

9. The non-transitory computer readable storage medium in accordance with claim 7, characterized in that the scattered light measurement takes place in reflection.

10. The non-transitory computer readable storage medium in accordance with claim 7, characterized in that the program carries out an image recognition of the at least one photograph.

11. The non-transitory computer readable storage medium in accordance with claim 7, characterized in that the at least one photograph is a photo of the drainage solution within the hose of a peritoneal dialysis machine.

12. The non-transitory computer readable storage medium at least in accordance with claim 11, characterized in that at least one marking is provided at the hose for the evaluation of the photograph of the drainage solution.

13. The non-transitory computer readable storage medium in accordance with claim 11, characterized in that two regions of the hose are evaluated by two of the at least one photograph, with one region corresponding to an inflow and one region corresponding to an outflow of a peritoneal dialysis machine.

* * * * *